United States Patent
Reuner

(10) Patent No.: US 6,361,509 B1
(45) Date of Patent: Mar. 26, 2002

(54) THERAPY APPARATUS WITH A SOURCE OF ACOUSTIC WAVES

(75) Inventor: Thomas Reuner, Erlangen (DE)

(73) Assignee: Siemans Aktiengesellschaft, Munich (DE)

(*) Notice: Subject to any disclaimer, the term of this patent is extended or adjusted under 35 U.S.C. 154(b) by 0 days.

(21) Appl. No.: 09/465,996

(22) Filed: Dec. 17, 1999

(30) Foreign Application Priority Data

Dec. 22, 1998 (DE) .......................................... 198 59 553

(51) Int. Cl.[7] ................................................. A61N 7/00
(52) U.S. Cl. .......................................... 601/2; 600/439
(58) Field of Search .......................... 601/2–4; 600/439, 600/407; 604/22

(56) References Cited

U.S. PATENT DOCUMENTS

| | | | | |
|---|---|---|---|---|
| 4,608,979 A | * | 9/1986 | Breidenthal et al. ........... 601/4 |
| 4,932,414 A | * | 6/1990 | Coleman et al. ............ 600/445 |
| 5,285,772 A | * | 2/1994 | Rattner ........................... 601/4 |
| 5,295,483 A | * | 3/1994 | Nowacki et al. ............ 600/439 |
| 5,435,311 A | * | 7/1995 | Umemura .................... 600/439 |
| 5,687,729 A | * | 11/1997 | Schaetzle .................... 600/439 |
| 5,699,804 A | * | 12/1997 | Rattner ....................... 600/439 |
| 5,810,748 A | * | 9/1998 | Ueberle ......................... 601/4 |

FOREIGN PATENT DOCUMENTS

| DE | 4120074 A1 | * | 1/1992 | ........... A61B/17/22 |
|---|---|---|---|---|
| DE | 29802888 U1 | * | 5/1998 | ......... A61B/17/225 |

* cited by examiner

Primary Examiner—Marvin M. Lateef
Assistant Examiner—Shawna J. Shaw
(74) Attorney, Agent, or Firm—Schiff Hardin & Waite

(57) ABSTRACT

A therapy apparatus has a source with an acoustic axis for generating acoustic waves converging in a focus lying on the acoustic axis. The source has a light generator that emits a focused light beam of visible light with a substantially parallel beam path that substantially coincides with the acoustic axis of the source and makes it visible.

11 Claims, 3 Drawing Sheets

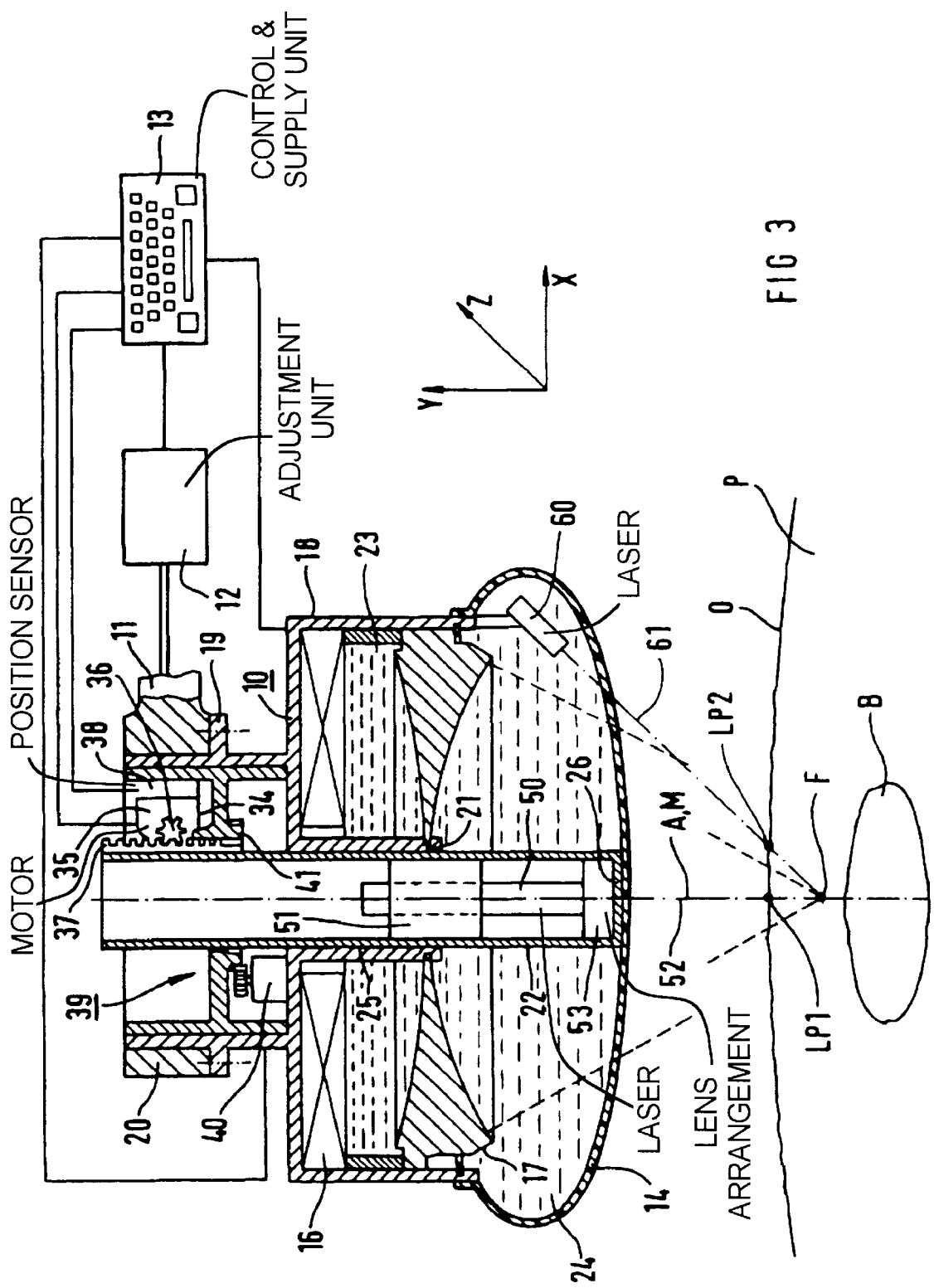

THERAPY APPARATUS WITH A SOURCE OF ACOUSTIC WAVES

BACKGROUND OF THE INVENTION

1. Field of the Invention

The present invention is directed to a therapy apparatus of the type having a source having an acoustic axis, which generates acoustic waves converging in a focus lying on the acoustic axis.

2. Description of the Prior Art

A therapy apparatus of the above type is utilized for disintegrating calculi in the body of a patient, for treating body tissue, for example tumor tissue, as well as in pain therapy and in osteo restoration.

In the utilization of such a therapy apparatus, there is the problem of aligning the source over the body surface of a patient such that the acoustic axis of the source proceeds substantially through the treatment area in the body of the patient.

The problem of aligning the source over the body surface of a patient is addressed in German PS 195 43 344 by providing the source with a guide tube at whose exterior end a light source is secured, with optics arranged at the other end inside the source. The guide tube is introduced into the source that a light beam from the light source illuminates the body surface of the patient and is supplied by the optics to a display arrangement via an optical conductor arranged in the guide tube. In this way, the source can be optically aligned, for example relative to a marking applied on the body surface of the patient, and under which the treatment area is located.

German PS 196 15 342 discloses a therapy apparatus of the type initially described wherein the source of the therapy apparatus has a light-transparent region through which the acoustic axis of the source proceeds. Optical means including a light source are arranged in the light-transparent region of the source for acquiring image information from the body surface of a patient to be treated. In this way the source can be optically aligned, for example relative to a previously marked region on the body surface of a patient under which the treatment area is located.

Both possibilities of optical alignment of the source over the body surface of a patient, however, have the disadvantage that the actual position of the acoustic axis on which the focus of the source to be aligned onto the treatment area is only approximately known to the person who aligns the source. Further measures are therefore required in order to align the acoustic axis of the source such that it proceeds through the treatment area of the patient and in order to displace the focus of the source on the treatment area.

SUMMARY OF THE INVENTION

An object of the present invention is to provide a source of the type initially described wherein the alignment of the acoustic axis of the source onto a treatment area lying in the interior of the body of a patient is simplified.

This object is inventively achieved in a therapy apparatus having a source with an acoustic axis, wherein the source has a light generator that emits a focused light beam of visible light having a substantially parallel (i.e. non-diverging) beam path that substantially coincides with the acoustic axis of the source and makes his axis visible. Because the focused beam of the light generator coincides with the acoustic axis and makes it visible, the position and the orientation of the acoustic axis of the source can always be recognized, for example for a physician treating the patient with the therapy apparatus. The focused light beam casts a light spot on the body surface of the patient to be treated, which can be brought into coincidence in a simple way by appropriate alignment of the source with, for example, a marking applied on the body surface of the patient that identifies the treatment area. Since the acoustic axis is visible as a result of the light beam, the orientation of the acoustic axis relative to the treatment area can always be monitored, and the source can be correspondingly aligned relative to the treatment area such that the acoustic axis in fact proceeds through the treatment area rather than only grazing it. Because the focused light beam of the light generator coincides with the acoustic axis and makes it visible, the position and the orientation of the acoustic axis of the source can always be recognized, for example for a physician treating the patient with the therapy apparatus. The focused light beam casts a light spot on the body surface of the patient to be treated, which can be brought into coincidence in a simple way by appropriate alignment of the source with, for example, a marking applied on the body surface of the patient that identifies the treatment area. Since the acoustic axis is visible as a result of the light beam, the orientation of the acoustic axis relative to the treatment area can always be monitored, an d the source can be correspondingly aligned relative to the treatment area such that the acoustic axis in fact proceeds through the treatment area rather than only.

In one embodiment of the invention the source has a light-transparent region through which the acoustic axis of the source proceeds and in which light generator is arranged. In this way, the focused light beam of the light generator can be brought into coincidence with the acoustic axis in an especially simple way so that it can be made visible.

In another version of the invention, the light generator is removable from the light-transparent region of the source. This provides the possibility of introducing other components as needed, for example a locator in the form of an ultrasound unit, into the light-transparent region of the source in order to exactly align the focus of the source onto the treatment area in the body of a patient, or in order to be able to determine or observe the course of the treatment during therapy.

In a further embodiment of the invention the light generator has optics arranged in the beam path of the focused light beam that influence the focused light beam such that configured light that provides information about the position of the focus relative to the surface can be generated on a surface onto which the focused light beam is directed. In this way, not only the position and orientation of the acoustic axis relative to a treatment area of a patient can be seen, but also the position of the focus along the acoustic axis relative to the body surface of the patient can be displayed, at least approximately. When, for example, the depth position of a treatment area in the inside of the body of a patient is known on the basis of examinations that have been implemented, for example palpation, not only can the acoustic axis be aligned as to position and orientation without additional auxiliaries, but also the focus can be aligned onto the treatment area in the interior of the body of the patient on the basis of the information derivable from the configured light imaged on the body surface.

In a version this embodiment the configured light forms rings generated with the optics, with each ring of the configured light providing information about the position of the focus relative to the surface. The rings can be projected in different image planes that the focused light beam penetrates substantially at a right angle, with at least one ring of the configured light being imaged optically sharp in an image plane. When, for example, the spacing of the source of acoustic waves changes relative to the body surface of a patient, rings, preferably having different diameters, are imaged on the body surface, with at least one ring being imaged optically sharp on the body surface dependent on the image plane in which the body surface lies. Depth information about the position of the focus in the body thus can be obtained on the basis of the sharpness of the imaging of a ring and on the basis of the diameter of the ring. Rings with larger diameter are preferably imaged optically sharp on the body surface the as the source comes closer to the body surface. In this way, the respective ring that is imaged optically sharp can still be recognized, given a source arranged comparatively close to the body surface but not covered by the source.

In a further embodiment of the invention, the source, in addition to the aforementioned light generator, has a second light generator that emits a focused light beam of visible light with a substantially parallel beam path, with the focused light beam from the second light generator intersects the focused light beam of the first means for generating light in the focus of the source. In this way, depth information as to the position of the focus in the body of a patient can be acquired. When the focus of the source lies below the body surface of a patient, then a first light point or spot on the body surface is produced by the first light generator, which identifies the position of the acoustic axis. A second light point or spot is projected on the body surface by the second light generator. Dependent on the angle that the two focused light beams describe, the distance of the light points from one another is an indication of the distance of the focus of the source from the body surface. When, for example, the two focused light beams describe an angle of approximately 45°, then the distance of the first light point on the body surface from the second light point on the body surface approximately corresponds to the distance of the focus of the source from the body surface. When the acoustic axis resides at a right angle relative to the body surface and when the two light points lie in the plane of the body surface, the distance indication is relatively exact.

In a preferred embodiment of the invention the first and/or the second light generator is/are a laser, that is especially suited for generating a focused light beam having a substantially coherent beam path.

DESCRIPTION OF THE DRAWINGS

FIG. 3 shows a further embodiment of an inventive therapy apparatus.

DESCRIPTION OF THE PREFERRED EMBODIMENTS

Figure 1:
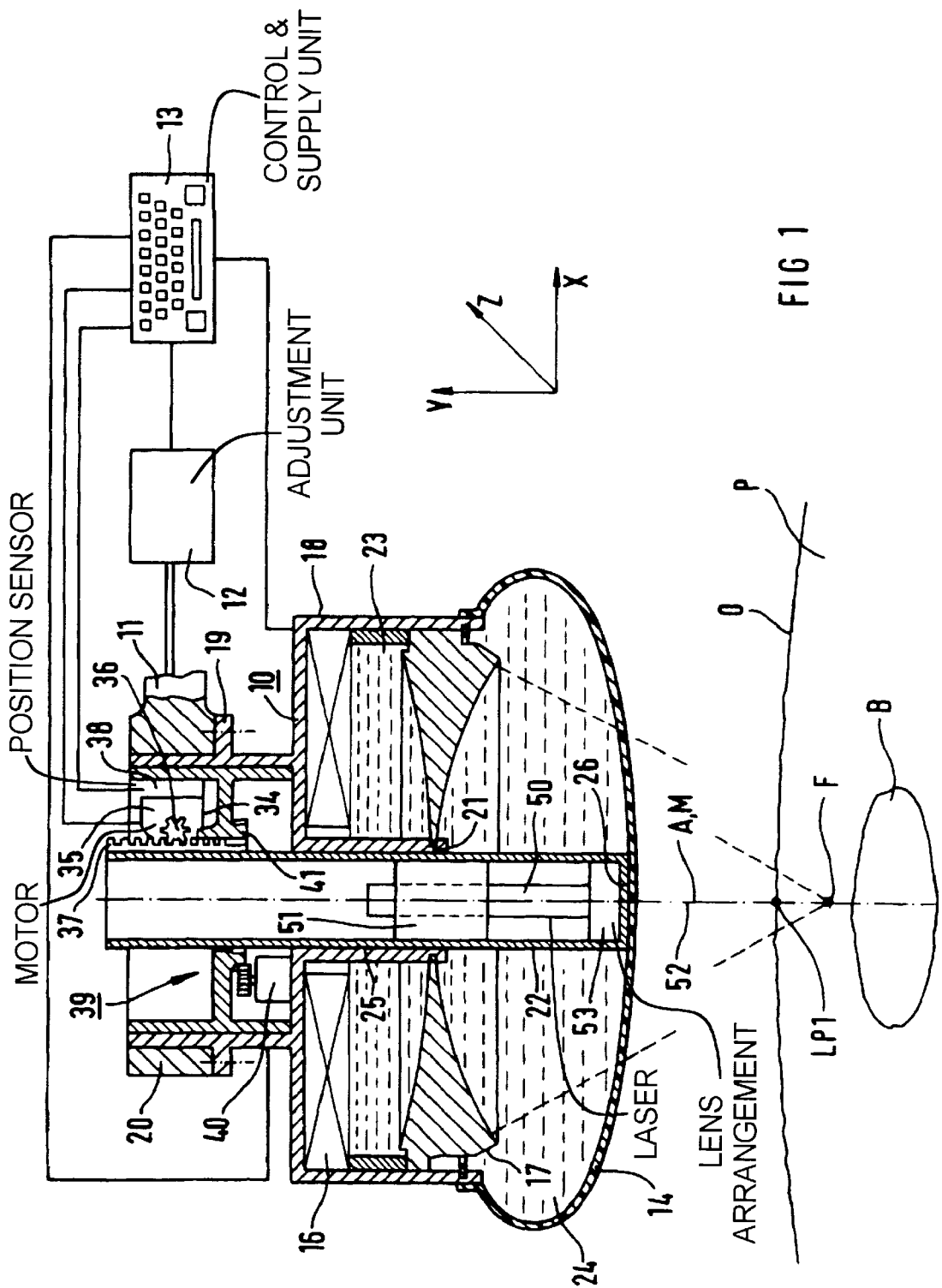
FIG. 1 shows an inventive therapy apparatus partially in section and partially as a block diagram.

As shown in FIG. 1, the inventive therapy apparatus has a source 10 of focused acoustic waves that is attached via a holder 11 to an adjustment unit 12, that is schematically indicated. This allows the adjustment of the source 10 in the direction of the axes X, Y, Z of the spatial coordinate system shown in FIG. 1. A control and supply unit 13 that contains all units needed for the operation of the source 10, and is provided with a keyboard 13 for operation of the therapy apparatus, is connected to the adjustment unit 12. The source 10 contains a central, light-transparent region, which is described in greater detail below, and is likewise provided with a light-transparent coupling membrane 14. The membrane 14 given treatment of a patient P with the source 10, lies against the body surface O of the patient P in order to be able to introduce the focused acoustic waves generated during operation of the therapy apparatus into the body of the patient P who, for example, is experiencing pain in a body region B.

As can be seen from FIG. 1, the source 10 of focused acoustic waves contains an electromagnetic pressure pulse source 16 (not shown in greater detail) and an acoustic positive lens 17. The positive lens 17 focuses the pressure pulses emanating from the pressure pulse source 16 onto a focus F, which is a matter of a spatial focus zone in practice. The focus F lies on the acoustic axis A of the source 10, which corresponds to the middle axis M of the source 10 with reference to which the source 10 is fashioned generally rotationally symmetric. The pressure pulse source 16 and the positive lens 17 are accepted in a housing 18 that has an end remote from the pressure pulse source 16 closed fluid-tight with the elastic, flexible coupling membrane 14. The high-voltage pulse generator required for the operation of the pressure pulse source 16 is a component of the operating and supply unit 13, to which the pressure pulse source 16 is connected via a corresponding line.

At its other end adjacent to the pressure pulse source 16, the housing 18 has a mounting flange 19 that secures the source 10 to a mounting ring 20 of the carrier 11 with the assistance of screws. Only the center lines of two screws are indicated with dashed lines in FIG. 1.

The space between the pressure pulse source 16 and the positive lens 17, as well as the space between the positive lens 17 and the coupling membrane 14, are filled with an acoustic propagation medium. In the exemplary embodiment, both spaces contain the same acoustic propagation medium, namely water 23 and 24. The two spaces filled with water 23 and 24 are separated from one another by the positive lens 17 in the exemplary embodiment. Particularly when both spaces contain the same acoustic propagation medium, however, they can be connected to one another.

The volume of the space between the positive lens 17 and the elastic and flexible coupling membrane 14 can be selectively enlarged or reduced—in a way that is not shown—by supplying water or removing water. When the coupling membrane 14 lies against the body surface of the patient P in a way that is not shown in FIG. 1, the position of the focus F can be set in this way relative to the body region B of a patient P to be treated.

A cup-shaped tube 22 is introduced in an opening 25 of a cylindrical tube-shaped inside wall 21 of the housing 18, the tube 22 being formed of a transparent material, at least in the region of its base 26, that preferably does not scatter light passing therethrough or only scatters it to a slight extent. The tube 22 is accepted so as to be axially displaceable and fluid-tight in the opening 25 of the inside wall 21. Sealant (not shown in FIG. 1) can be provided.

The opening 25 of the source 10 within the inside wall 21, through which the middle axis M of the source 10 proceeds centrally and in which the tube 22 is located, represents the aforementioned, light-transparent region from which the water 24 is displaced with the tube 22. The tube 22 is displaceably arranged in the opening 25 of the inside wall 21 such that its base 26, when the source 10 is applied to the body surface O of the patient P, can be placed against the body surface O of the patient P with the interposition of the coupling membrane 14, such placement not being shown in FIG. 1. To this end, an adjustment unit 34 is provided with which the tube 22 is adjustable in the direction of the acoustic axis A. The adjustment unit 34 contains an electric motor 35 provided with a gear pinion 36 that interacts with a toothed rack 37 provided at the tube 22. The adjustment unit 34 has a position sensor 38 allocated to it that supplies a signal corresponding to the axial position of the tube, this signal being supplied to the operating and supply unit 13 via a signal line. In this way, the current position of the tube 22 can always be monitored from the operating and supply unit 13 and a desired position of the tube 22 can be set.

With an adjustment unit 39, the tube 22 can also be rotated around the acoustic axis A. The adjustment unit 39 contains an electric motor 40 provided with a gear pinion that interacts with a component provided with a toothed gear rim 41, this component being rotatably accepted in the housing 18, and a toothed rack 37 engaging a channel of this component being c-rotatably connected to the tube 22.

The electric motors 35 and 40 of the adjustment units 34 and 39 are connected to the operating and supply unit 13 via corresponding lines.

In the exemplary embodiment, a light generator is introduced in the tube 22, which emits a focused light beam of visible light with a substantially parallel beam path. In the exemplary embodiment, the light generator is a laser 50, which is accepted in the tube 22 by a holder 51 matched to the inside wall of the tube 22, so that a laser light beam 52 of focused visible light emanating from the laser 50 coincides with the acoustic axis A of the source 10. The laser light beam 52 has a beam diameter of approximately 5 mm or less, so that the acoustic axis A of the source 10 can be easily seen. The laser light beam 52 generates a laser light point or spot LP1 on the body surface O of the patient P. On the basis of the laser light point LP1, the source 10 can be aligned over the body surface O of the patient P in a simple way with the operating and supply unit 13, for example to a marking (not visible in FIG. 1) that was applied to the body surface O of the patient P in a preliminary examination, so that the laser light point LP1 is brought into coincidence with the marking. Moreover, the acoustic axis A, which is visible as a result of the laser light beam 52, can be monitored as to its orientation relative to the body region B to be treated and can be aligned such by adjustment movements of the source 10 so that the acoustic axis A proceeds through the body region B to be treated.

In the process of alignment of the source 10 over the body surface O of a patient P, the tube 22 preferably is seated against the coupling membrane 14 in order to avoid dispersion of the laser light beam 52 through the water 24 insofar as possible. During the alignment, however, the tube 22 need not necessarily be brought into a position seated against the coupling membrane 14.

When the laser light point LP1 of the laser light beam 52 has been brought into coincidence with the marking on the body surface O of the patient P and the acoustic axis A of the source 10 has been aligned to the body region B of the patient P to be treated, the focus F of the source 10 can be displaced onto the body region B to be treated, using the operating and supply unit 13. The displacement of the focus F of the source 10 onto the body region B can ensue by an adjustment of the source 10, by an adjustment of the patient P, or by a combined adjustment thereof relative to one another, in the direction of the acoustic axis A.

In order to facilitate the displacement of the focus F along the acoustic axis onto the body region B, optics in the form of a lens arrangement 53 is allocated to the laser 50 in the exemplary embodiment, the lens arrangement 53 influencing the laser light beam 52 emanating from the laser 50 so as to produce configured light on the body surface O of the patient P, that provides information about the position of the focus F relative to the body surface O of the patient P.

In the exemplary embodiment, the lens arrangement 53 generates configured light in the form of rings. The lens arrangement 53 constructed so that rings of different diameters are projected in various image planes parallel to one another, which the laser light beam 52 penetrates substantially at a right angle. At least one ring of the configured light is imaged optically sharp in an image plane.

Figure 2:
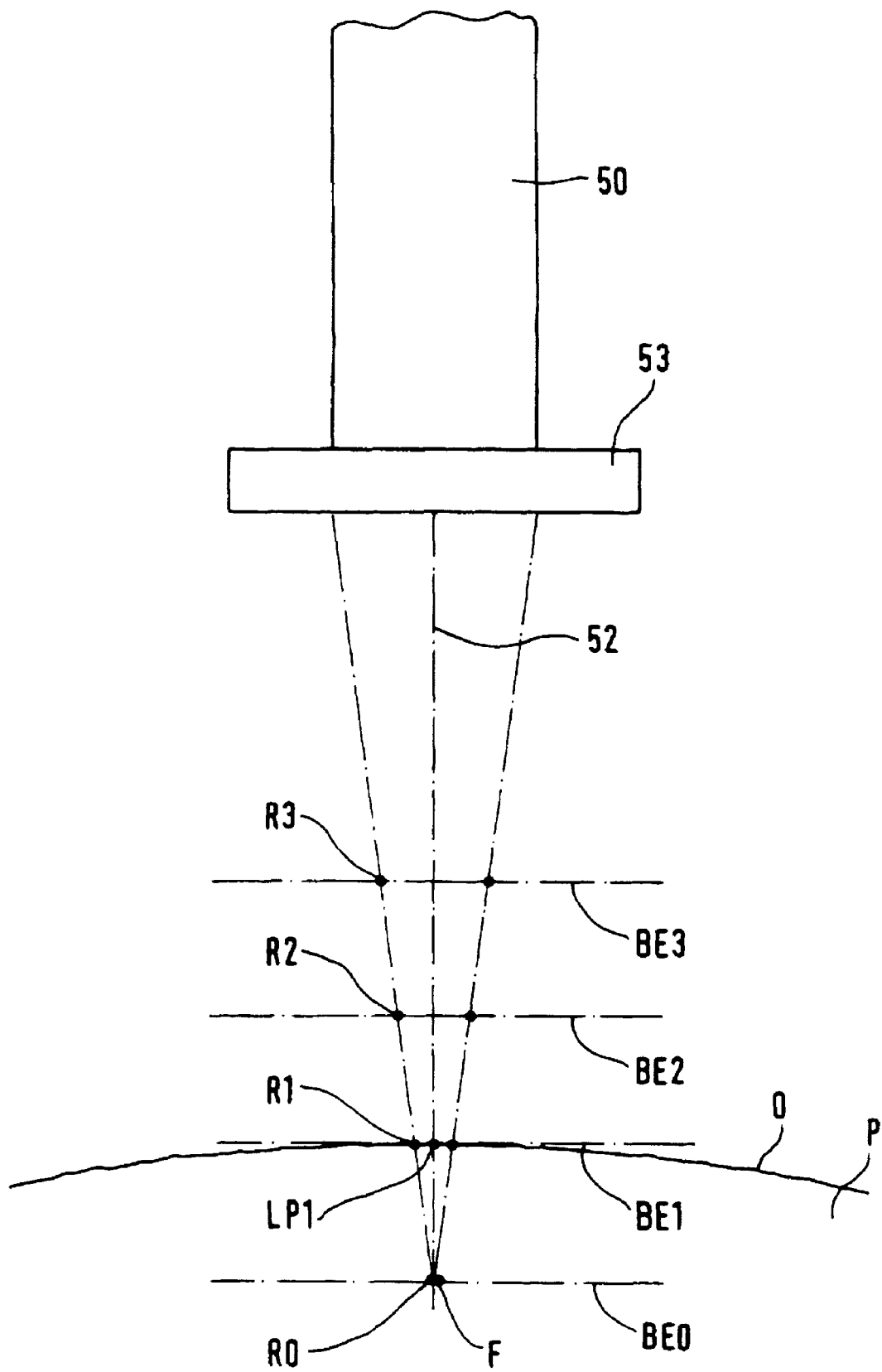
FIG. 2 illustrates the imaging of rings in various image planes in accordance with the invention.

FIG. 2 illustrates the imaging of rings R0 through R3 in various image planes BE0 through BE3. Only the laser 50 and the lens arrangement 53 from FIG. 1 are shown in FIG. 2. The lens arrangement 53 is designed such that the laser light beam 52 always remains visible, and thus identifies the optical axis A of the source 10. Additionally, rings R0 through R3 are imaged optically sharp in image planes BE0 through BE3. The ring R0 imaged in the image plane BE0 surrounds the laser light beam 52 and identifies the focus F of the source 10. When, as shown in FIG. 2, the body surface O of the patient P comes to lie in the image plane BE1, the ring R1 is imaged optically sharp onto the body surface O of the patient P.

Since the rings R0 through R3 are generated in a geometrically specific way, i.e. so that the image planes BE0 through BE3 in which the rings R0 through R3 are imaged optically sharp exhibit fixed and geometrically defined spacings from one another and so that the focus F of the source 10 lies in the image plane BE0, each of the rings R0 through R3 imaged on the body surface O of the patient provides depth information about the position of the focus F of the source 10.

In order to be able to derive such depth information from the rings imaged on the body surface O, the laser 50 and the lens arrangement 53 must be arranged in the source 10 in a defined way. In the exemplary embodiment, the lens arrangement 53 is arranged on the base 26 of the tube 22 and the laser 50 is arranged directly above the lens arrangement 53 in the tube 22. The tube 22 is located in a defined position within the opening 25 of the source 10. This position of the tube 22 can be set with the operating and supply unit 13 during the alignment of the source 10 over the body surface O of the patient P, as a result of which a relationship is produced between the source 10 (or the position of the focus F of the source 10) and the laser 50 and the lens arrangement 53 so that the focus F lies in the image plane BE0.

The imaging of the rings R0 through R3 preferably ensues such that the diameter of the ring imaged at the greatest distance from the source 10, i.e. the diameter of the ring R0 imaged optically sharp in the image plane BE0, is the smallest, and the diameter of the ring imaged closest to the source 10, i.e. the diameter of the ring R3 imaged optically sharp in the image plane BE3, is the largest. In this way, the ring R3 is still visible even when the source 10 is arranged relatively close to the body surface O of the patient P and is not completely covered by the source 10. As can be seen from FIG. 2, a type of light cone arises when the rings R0 through R3 are connected (by imaginary lines).

In one version of the light configuration, for example, the image planes BE0 through BE3 have a spacing of 1 cm from one another and the rings R0 through R3 imaged optically sharp in the respective image planes BE0 through BE3 have a diameter substantially corresponding to the depth position of the focus F relative to the image plane. In such version, the distance of the ring R3 imaged in the image plane BE3 would amount to approximately 3 cm from the focus F and the diameter thereof thus would amount to approximately 3 cm.

This arrangement of the image planes BE0 through BE3 and their spacings from one another, however, is only an example. More or fewer image planes and rings imaged optically sharp therein can be generated. When expedient, the configured light need not necessarily include rings, but can include other structures. The lens arrangement 53 is designed in conformity with the desired form of configured light and the elements thereof to be imaged in the image planes.

When the focus F of the source 10 has been displaced onto the body region B to be treated using the rings R0 through R3, the source can be seated against the body surface O of the patient P via the coupling membrane 14 with the operating and supply unit 13 in order to be able to introduce the acoustic waves into the body of the patient P. This occurs by increasing the volume of the space between the coupling membrane 14 and the positive lens 17, with sufficient water 24 being supplied to the space so that the elastic coupling membrane 14 lies flush against the body surface O of the patient P.

FIG. 3 shows another embodiment of the therapy apparatus, wherein the source 10 is provided with second light generator that likewise emit a focused light beam of visible light with a substantially parallel beam path. This second light generator also cab be a laser 60 that emits a focused laser light beam 61 of visible light. The laser 60 in the exemplary embodiment is arranged at an extension of the housing 18, in the space between the coupling membrane 14 and the positive lens 17, so that the laser light beam 61 of the laser 60 and the laser light beam 52 of the laser 50 intersect in the focus F of the source 10. In the exemplary embodiment, these beams approximately describe a 45° angle with one another. The laser 50 can thereby be located at an arbitrary position in the tube 22, but must be oriented such that the laser light beam 52 coincides with the acoustic axis A of the source 10. In the exemplary embodiment, the laser 60 is designed fluid-tight, so that it can be disposed in the space between the coupling membrane 14 and the positive lens 17, preferably outside the transmission region of the shock waves indicated with broken lines in FIG. 3.

As in the way described above, an alignment of the source 10 over the body surface O of the patient P is possible on the basis of the laser light beam 52. Further, the orientation of the acoustic axis A relative to the treatment region B in the inside of the body of the patient P can be monitored on the basis of the laser light beam 52 and can be correspondingly set with the operating and supply unit 13. Using the second laser light beam 61, moreover, depth information about the position of the focus F on the acoustic axis A can be acquired. When the focus F is located outside the body of the patient P, the focus F can be recognized as the intersection of the laser light beams 52 and 61. When the focus F is located inside the body of the patient P, as shown in FIG. 3, the laser light beam 52 generates a first laser light point LP1 on the body surface O through which the acoustic axis A proceeds, and the laser light beam 61 generates a second laser light point LP2 on the body surface of the patient P that differs from the laser light point LP1. The distance of the laser light points LP1 and LP2 from one another thus is an indicator for the position of the focus F in the inside of the body of the patient P on the acoustic axis A. If the laser light beams 52 and 61 describe a 45° angle with one another, the spacing of the laser light points LP1 and LP2 given the position of the source 10 relative to the body surface O of the patient P shown in FIG. 3, corresponds relatively exactly to the distance of the focus F from the body surface O of the patient P. This is thus the case when the acoustic axis A resides approximately at a right angle on the body surface O of the patient P, and the laser light points LP1, LP2 lie in the plane of the body surface O. Thus depth information about the position of the focus F on the acoustic axis A also can be acquired in this way.

The laser 60 need not necessarily be arranged in the space between the coupling membrane 14 and the positive lens 17. The laser 60 can alternatively be arranged at the exterior, for example above a holder attached to the housing 18 such that the laser light beams 52 and 61 describe a 45° angle with one another and intersect in the focus F of the source 10.

The tube 22 as well as the laser 50 and the lens arrangement 53 can, moreover, be removed as needed from the source 10 of acoustic waves, but it must be assured that a corresponding tube is introduced into the source 10 (in a way that is not shown) in order to prevent escape of the water 24.

Instead of mounting the laser 50 in the tube 22, the laser 50 can be directly arranged in the light-transparent region of the source 10. In this case, the laser 50 must also be designed fluid-tight.

If the source 10 does not have a light-transparent region, the laser 50 is arranged in the source 10, for example at the positive lens 17 of the source 10, so that the laser light beam emitted by the laser 50 coincides with the acoustic axis of the source.

In the exemplary embodiment, the tube 22 is moved in the opening 25 of the inside wall 21 of the housing 18 by means of the adjustment units 38 and 39. The tube 22, however, alternatively can be manually moved in a corresponding way.

In the exemplary embodiments described above, further, the source 10 contains an electromagnetic pressure pulse source. The inventive therapy apparatus, however, alternatively can contain a different type of pressure pulse source, for example a piezoelectrically functioning pressure pulse source. Moreover, there is the possibility of providing other sources of acoustic waves instead of a pressure pulse source, for example an ultrasound source that generates ultrasound in the form of continuous sound, ultrasound bursts or ultrasound pulses.

Moreover, there is also the possibility of implementing the alignment of the source 10 over the body surface O of the patient P manually, instead of using the operating and supply unit 13.

Although modifications and changes may be suggested by those skilled in the art, it is the intention of the inventor to embody within the patent warranted hereon all changes and modifications as reasonably and properly come within the scope of his contribution to the art.

I claim as my invention:

1. A therapy apparatus comprising:
   a source of acoustic waves, having an acoustic axis and including an arrangement for focusing said acoustic waves to converge in a focus disposed on said acoustic axis; and
   a light generator mounted to said source of acoustic waves which emits a focused, substantially parallel beam of visible light that substantially coincides with said acoustic axis and which makes a linear portion of said acoustic axis visible.

2. A therapy apparatus as claimed in claim 1 wherein said source of acoustic waves comprises a light-transparent region through which said acoustic axis proceeds, and wherein said light generator is mounted in said light-transparent region of said source of acoustic waves.

3. A therapy apparatus as claimed in claim 2 wherein said light generator is removably mounted in said light-transparent region.

4. A therapy apparatus as claimed in claim 1 further comprising optics disposed in said substantially parallel beam path of said visible light for interacting with said visible light in said substantially parallel beam path to produce configured light which provides information about a position of said focus relative to a surface of a patient to be treated with said source of acoustic waves, said optics being adapted to project said configured light onto said surface, and said substantially parallel beam path of said visible light also being incident on said surface.

5. A therapy apparatus as claimed in claim 4 wherein said optics generates configured light comprising a plurality of rings, said rings providing said information about the position of said focus relative to said surface.

6. A therapy apparatus as claimed in claim 5 wherein said optics generates said rings with respectively different depths of focus so that said rings are respectively imaged optically sharp in different image planes, and wherein said substantially parallel beam path of said visible light proceeds through said image planes substantially at a right angle.

7. A therapy apparatus as claimed in claim 1 wherein said light generator is a first a light generator and wherein said substantially parallel beam path of visible light comprises a first substantially parallel beam path of visible light, and wherein said therapy apparatus further comprises a second light generator, which emits a focused, second light beam of visible light proceeding along a second substantially parallel beam path which intersects said first substantially parallel beam path.

8. A therapy apparatus as claimed in claim 7 wherein said first light generator comprises a laser.

9. A therapy apparatus as claimed in claim 7 wherein said second light generator comprises a laser.

10. A therapy apparatus as claimed in claim 7 wherein said first light generator comprises a first laser and wherein said second light generator comprises a second laser.

11. A therapy apparatus as claimed in claim 1 wherein said light generator comprises a laser.

* * * * *